(12) United States Patent
Zhang et al.

(10) Patent No.: US 7,658,754 B2
(45) Date of Patent: Feb. 9, 2010

(54) METHOD FOR THE CORRECTION OF SPINAL DEFORMITIES USING A ROD-PLATE ANTERIOR SYSTEM

(75) Inventors: Hong Zhang, Plano, TX (US); Charles E. Johnston, II, Dallas, TX (US); William A. Pierce, Dallas, TX (US); Richard B. Ashman, Navarre, FL (US)

(73) Assignee: Warsaw Orthopedic, Inc.

( * ) Notice: Subject to any disclaimer, the term of this patent is extended or adjusted under 35 U.S.C. 154(b) by 323 days.

(21) Appl. No.: 11/368,001

(22) Filed: Mar. 3, 2006

(65) Prior Publication Data

US 2006/0235390 A1    Oct. 19, 2006

Related U.S. Application Data

(63) Continuation of application No. PCT/US2004/028690, filed on Sep. 3, 2004.

(60) Provisional application No. 60/500,187, filed on Sep. 4, 2003.

(51) Int. Cl.
*A61B 17/70* (2006.01)
(52) U.S. Cl. .................. 606/264; 606/246; 606/279; 606/282

(58) Field of Classification Search ............. 606/61, 606/69, 105, 246–279, 281–299, 70, 71; 623/17.11
See application file for complete search history.

(56) References Cited

U.S. PATENT DOCUMENTS

| | | | | |
|---|---|---|---|---|
| 5,084,049 | A | | 1/1992 | Asher et al. |
| 5,324,290 | A | * | 6/1994 | Zdeblick et al. ............... 606/61 |
| 5,549,607 | A | * | 8/1996 | Olson et al. ................... 606/61 |
| 6,214,006 | B1 | * | 4/2001 | Metz-Stavenhagen ......... 606/61 |
| 6,261,287 | B1 | * | 7/2001 | Metz-Stavenhagen ......... 606/61 |
| 6,569,164 | B1 | | 5/2003 | Assaker et al. |
| 6,585,738 | B1 | * | 7/2003 | Mangione et al. ............. 606/61 |
| 6,682,532 | B2 | * | 1/2004 | Johnson et al. ............... 606/73 |

* cited by examiner

*Primary Examiner*—Thomas C Barrett
*Assistant Examiner*—Andrew Yang

(57) ABSTRACT

An anterior instrumentation method of treating spinal deformities involves a combination of a spinal rod anterior system and one or two spinal plates fixed on the cephalad and caudal end vertebrae of the instrumented segment. Deformities are treated by the anterior rod system through compression, distraction and derotation. Two spinal plates are fixed to the cephalad and caudal end vertebrae respectively to prevent the end vertebrae from rotating into kyphosis. A number of cancellous screws are inserted into the cephalad and caudal end vertebrae and their adjacent vertebrae through the spinal plate to provide several points of fixation on the end vertebrae to prevent implant failure and loss of correction.

34 Claims, 16 Drawing Sheets

METHOD FOR THE CORRECTION OF SPINAL DEFORMITIES USING A ROD-PLATE ANTERIOR SYSTEM

CROSS REFERENCE TO RELATED APPLICATIONS

The present application is a continuation of International PCT Application No. PCT/US2004/028690, filed on Sep. 3, 2004 and published on Mar. 17, 2005 as International Publication No. WO 2005/023090, which claims the benefit of U.S. Provisional Application No. 60/500,187, filed on Sep. 4, 2003, the entire contents of each application hereby being incorporated by reference.

FIELD OF THE INVENTION

The present invention concerns an anterior spinal instrumentation system which allows two spinal plates at the cephalad and caudal end vertebrae to be combined with a rod-type anterior system. The rod-plate anterior system will be used for the surgical management of thoracolumbar and lumbar scoliosis and other situations requiring spinal stabilization.

BACKGROUND

Dwyer first introduced spinal instrumentation for anterior spinal fusion in 1969. The Dwyer system used screws and a flexible cable. However, this system merely provided limited stability by the compressive effect of the one vertebral body against the other. The flexible cable resisted only tension forces, and the inability of the Dwyer system to provide a rigid connection between vertebrae often led to cable or screw failure with subsequent pseudarthrosis. In 1976 Zielke modified the Dwyer system by substituting a small diameter threaded rod and nuts for the cable and introduced a derotator designed to correct rotation and to prevent kyphosis. Over time, the Zielke instrumentation procedure for management of thoracolumbar and lumbar scoliosis was recognized to have significant advantages over the Dwyer system in terms of effective correctability of the coronal curvature, the ability to correct deformity by instrumenting shorter segments of the spine and also its derotation capability. However, the Zielke instrumentation has been reported to have high incidence of implant breakage, loss of correction, progression of the kyphosis, and pseudarthrosis caused primarily by lack of segmental stiffness in the relatively small diameter rod.

With the introduction of a larger diameter solid rod system by TSRH in 1989, creation of lordosis in the instrumented segment was possible by the appropriate contouring and rotation of a larger diameter rod. The 300% to 400% increased stiffness of the 6.4 mm rod over that of the Dwyer or Zielke longitudinal members was expected to provide stiffness sufficient to increase fusion rates while maintaining correction without external immobilization. However, after review of cases performed with the instrumentation, the incidence of loss of correction in both frontal and sagittal planes remained unacceptable, though improved compared to Dwyer and Zielke.

Some authors documented significantly high strains at the bone-screw interface of the cephalad and caudal end vertebral screws. Loss of correction and kyphosis in the single rod instrumented segment probably resulted from insufficient construct stiffness in the early postoperative period as a consequence of bone-screw interface loosening, especially at the cephalad and caudal interspaces. The single rigid rod may provide sufficient stability for the correction of the deformed spine during the early postoperative period. However, it may not prevent the vertebral rotation about each screw axis at the bone-screw interface during everyday activity. The possible reason is that the single solid rod system lacks two fixation points on each vertebra, particularly in the most cephalad and caudal end vertebrae of the instrumented segment.

In 1996, Kaneda introduced a two-rod anterior system (KASS) with two fixation points on each vertebra for management of thoracolumbar and lumbar scoliosis. The KASS system seemed to address some of the problems associated with prior systems, preventing the end vertebrae from rotating into kyphosis. This technique has been performed with good results in the early follow-up period. However, this system has some limitations; namely, the system has a high prominent profile and is difficult to apply to a severely deformed spine.

To combine the relative ease of implanting a single rigid rod structure with two fixation points on each end vertebra, the rod-plate anterior system of the present invention is an improvement over the single solid rod anterior system (TSRH), and also allows spinal plate fixation at the cephalad and caudal end vertebrae of the instrumentation segment.

SUMMARY

The present invention provides a rod-plate spinal anterior instrumented system having an improved single rigid rod anterior system to allow spinal plate fixation at the cephalad and caudal end vertebrae in the instrumented segment. Additionally, the present invention combines the relative advantages of a rod based anterior instrumentation with plates to increase bone implant strength and stability.

BRIEF DESCRIPTION OF THE DRAWINGS

FIG. 2e is a side cross-sectional view of the L-shape spinal plate illustrated in FIG. 2a, as taken along line 2e-2e of FIG. 2a.

FIG. 2f is a side cross-section view of the L-shape spinal plate illustrated in FIG. 2a, as taken along line 2f-2f of FIG. 2a.

FIG. 7c is a top view of a pair of vertebral staples with a lower profile compared to those illustrated in FIG. 7a.

FIG. 13c a side cross-section view of the rectangular spinal plate illustrated in FIG. 13a, as taken along line 13c-13c of FIG. 13a.

DESCRIPTION OF THE PREFERRED EMBODIMENTS

Figure 1A:
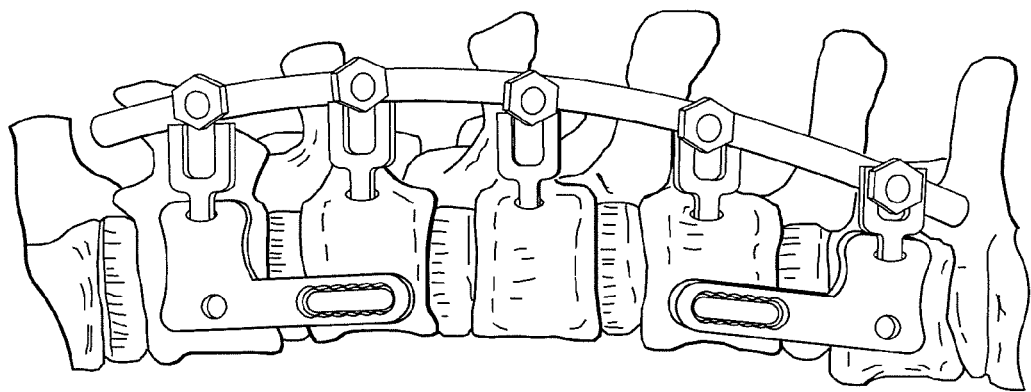
FIG. 1a is a representation of the thoracolumbar spine with a rod-plate anterior system.
Figure 1B:
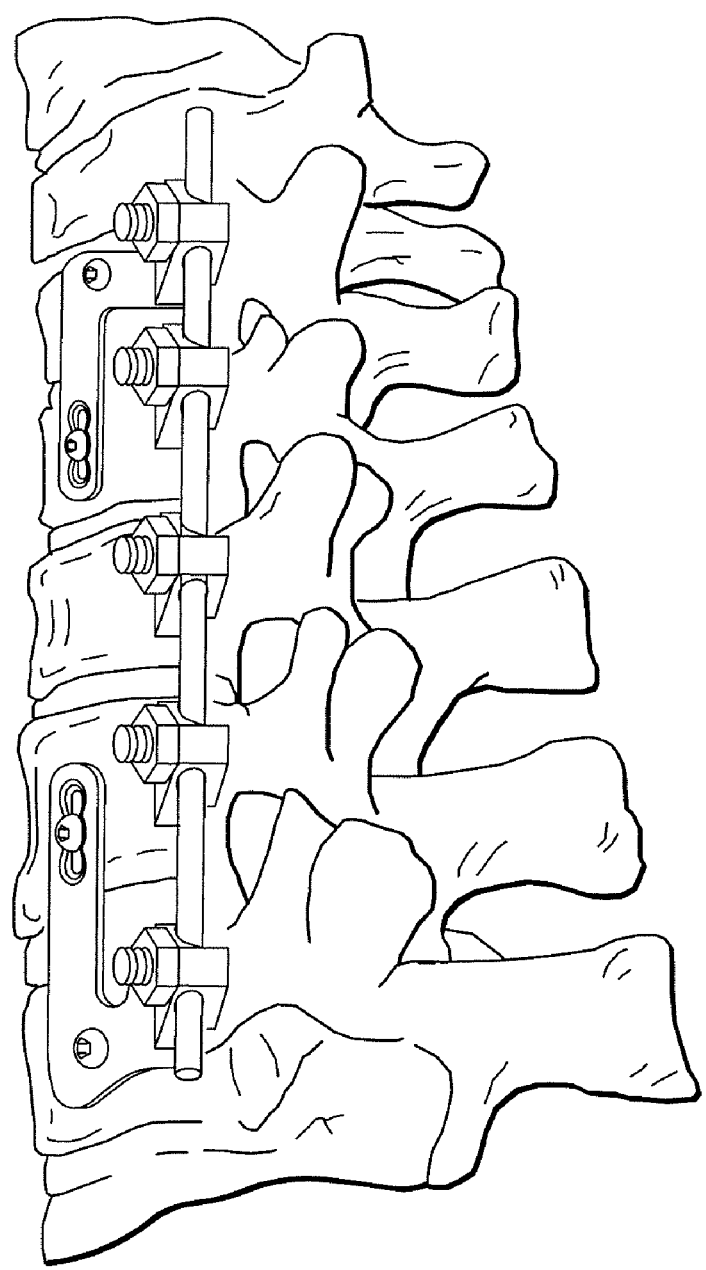
FIG. 1b is a representation of the thoracolumbar spine with the rod-plate anterior system.
Figure 2A:
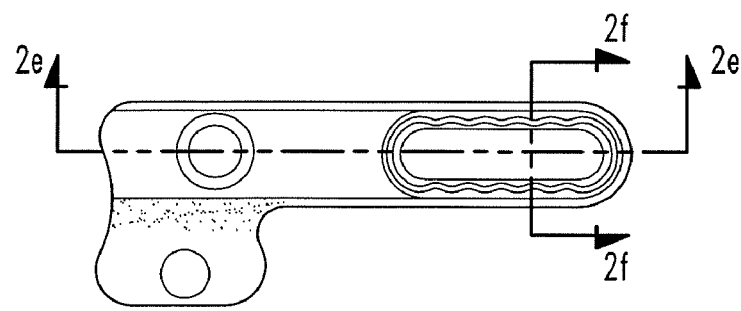
FIG. 2a is a top view of an L-shaped spinal plate in accordance with one embodiment of the invention, as depicted in FIG. 1b.
Figure 2B:
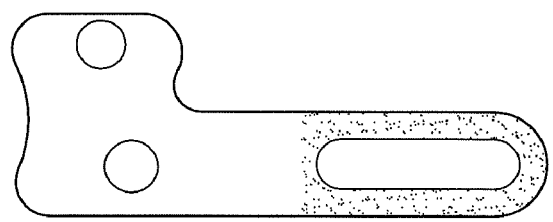
FIG. 2b is a bottom view of an L-shape spinal plate.
Figure 2C:
FIG. 2c is a front view of an L-shape spinal plate.
Figure 2D:
FIG. 2d is a lateral view of an L-shape spinal plate.
Figure 2E:
Figure 2F:
Figure 3A:
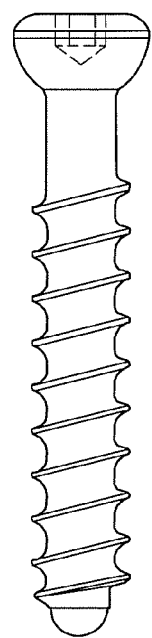
FIG. 3a is a side view of an embodiment of a cancellous bone screw for use with present invention.
Figure 3B:
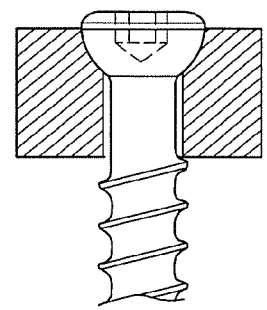
FIG. 3b is a cross-sectional view of the bone screw illustrated in FIG. 3a, as used in association with a spinal plate.
Figure 4:
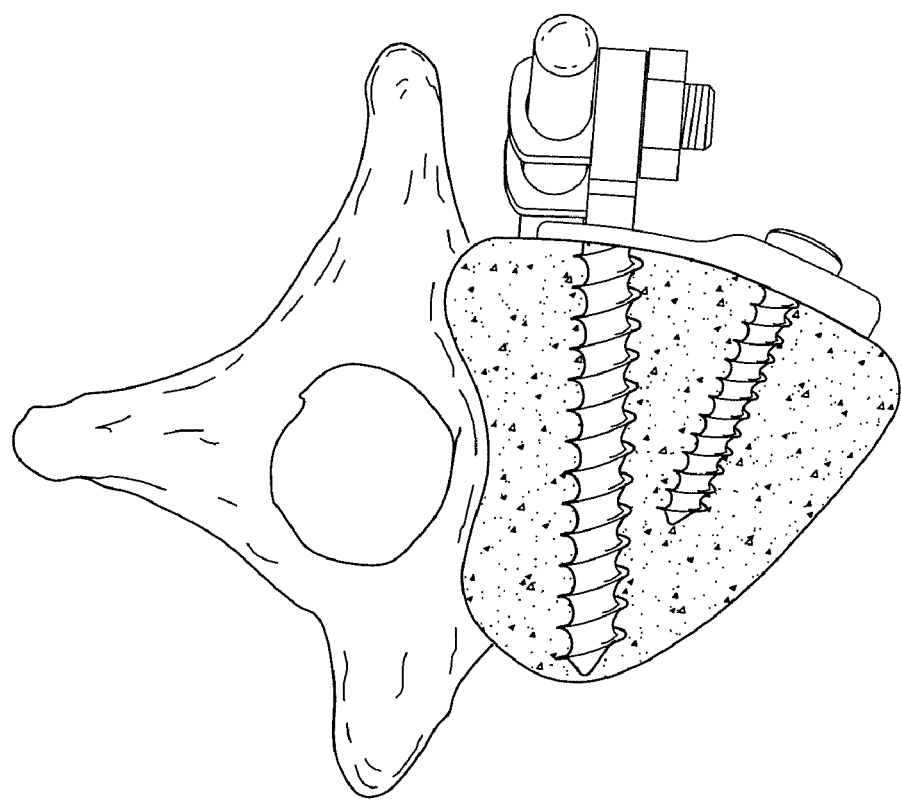
FIG. 4 is a side cross-sectional view of the end vertebra fixation illustrated in FIG. 1b, showing a stable triangular construct of the end vertebra between the two screws and the transverse portion of the spinal plate.
Figure 5:
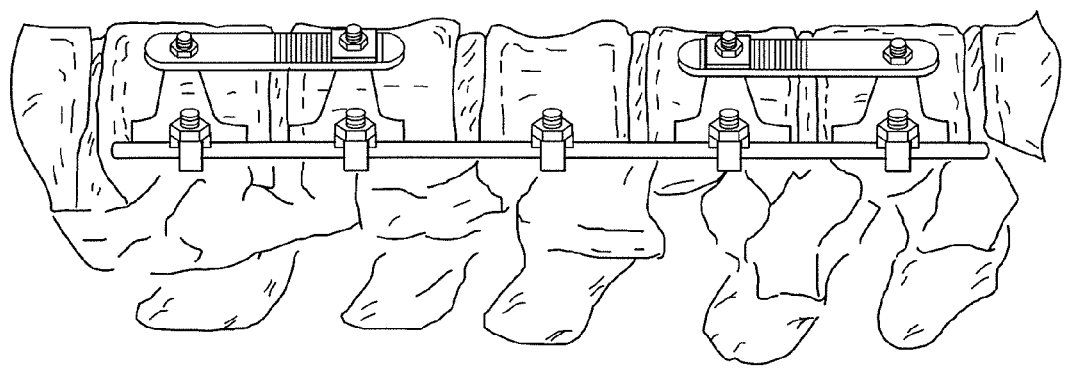
FIG. 5 is a representation of the thoracolumbar spine and another embodiment of the rod-plate anterior system.
Figure 6A:
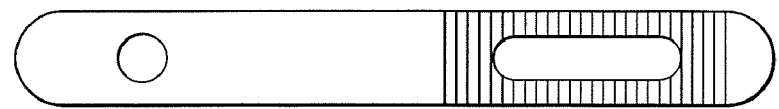
FIG. 6a is a top view of a rectangular-shaped spinal plate in accordance with the embodiment of the invention illustrated in FIG. 5.
Figure 6B:
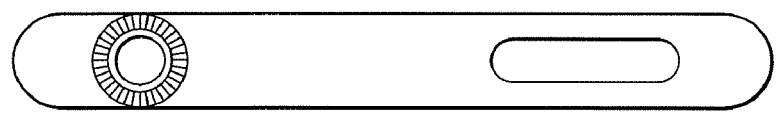
FIG. 6b is a bottom view of a rectangular-shape spinal plate.
Figure 6C:
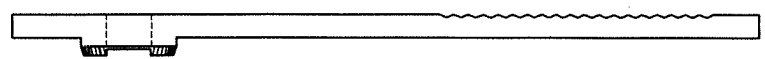
FIG. 6c is a frontal view of a rectangular-shape spinal plate.
Figure 7A:
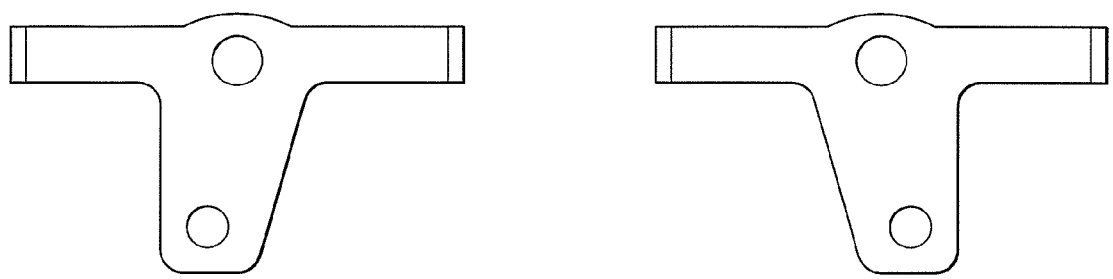
FIG. 7a is a top view of a pair of vertebral staples in accordance with one embodiment of the invention, as illustrated in FIG. 5.
Figure 7B:
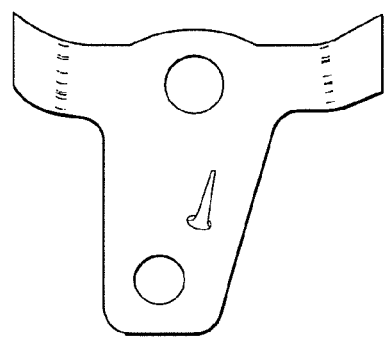
FIG. 7b is a bottom view of vertebral staple.
Figure 7C:
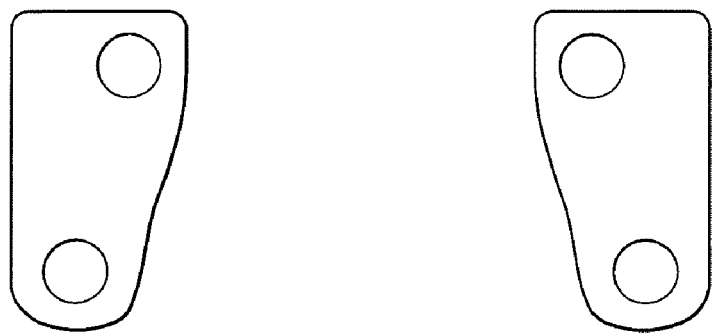
Figure 7D:
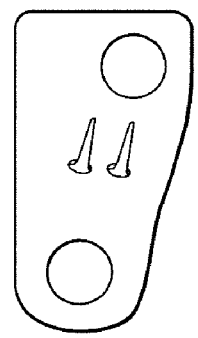
FIG. 7d is a bottom view of a vertebral staple.
Figure 8A:
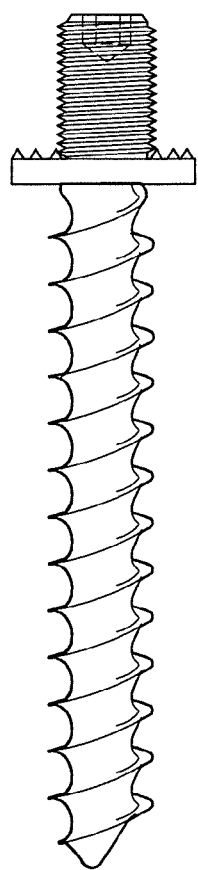
FIG. 8a is a side view of an embodiment of a bone screw with a serration-wall junction in accordance with one embodiment of the invention, as illustrated in FIG. 5.
Figure 8B:
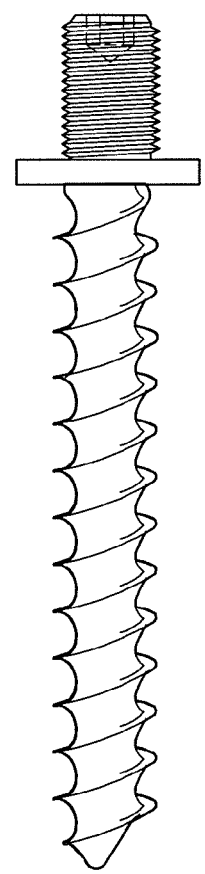
FIG. 8b is a side view of an embodiment of a bone screw with a plain-wall junction in accordance with one embodiment of the invention, as illustrated in FIG. 5.
Figure 9A:
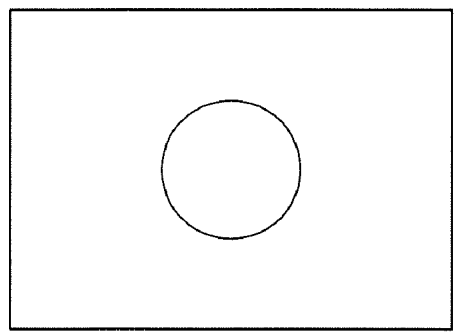
FIG. 9a is a top view of a serration-washer in accordance with one embodiment of the invention, as illustrated in FIG. 5.
Figure 9B:
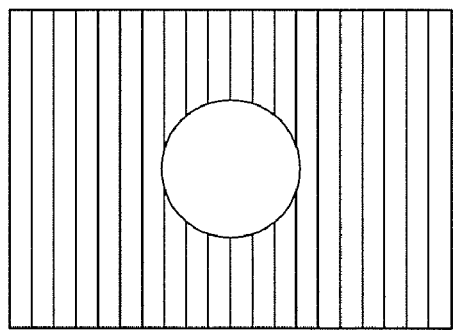
FIG. 9b is a bottom view of a serration-washer in accordance with one embodiment of the invention, as illustrated in FIG. 5.
Figure 9C:
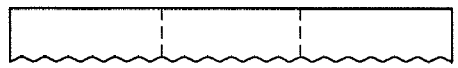
FIG. 9c is a front view of a serration-washer in accordance with one embodiment of the invention, as illustrated in FIG. 5.
Figure 10:
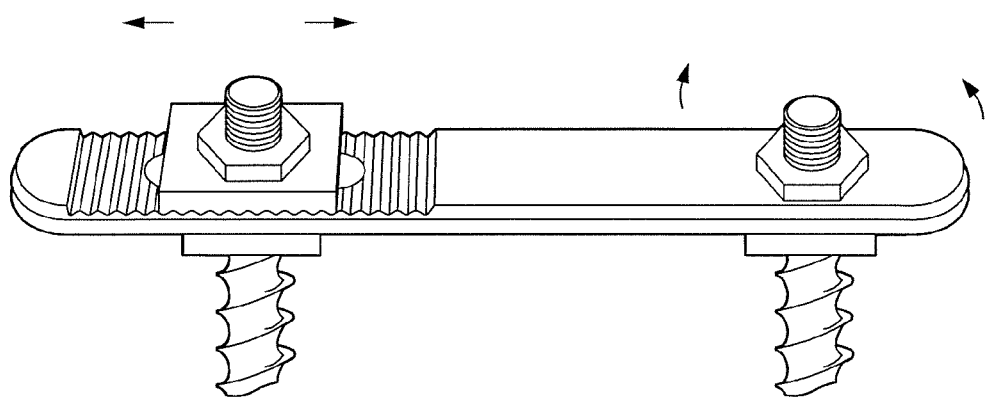
FIG. 10 is a representation of spinal plate, bone screws, washer and nuts in accordance with one embodiment of the invention, as illustrated in FIG. 5, showing that the spinal plate can mount to a bone screw in varying angular orientations and with variable positions to match the adjacent bone screw.
Figure 11:
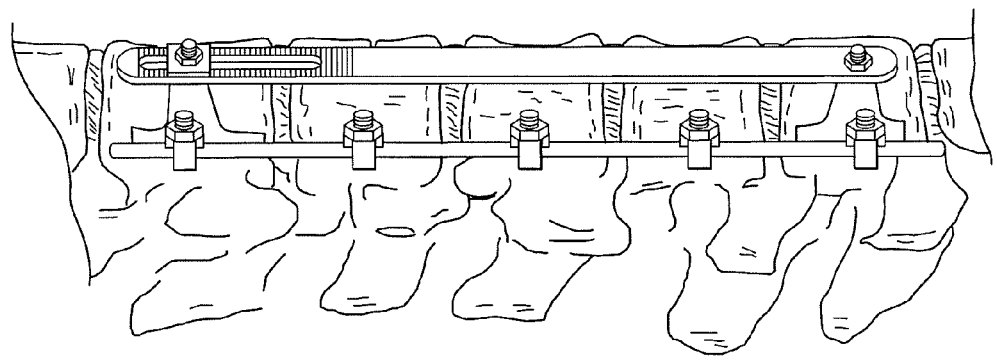
FIG. 11 is a representation of the thoracolumbar spine with another rod-plate anterior system similar to the system illustrated in FIG. 5.
Figure 12:
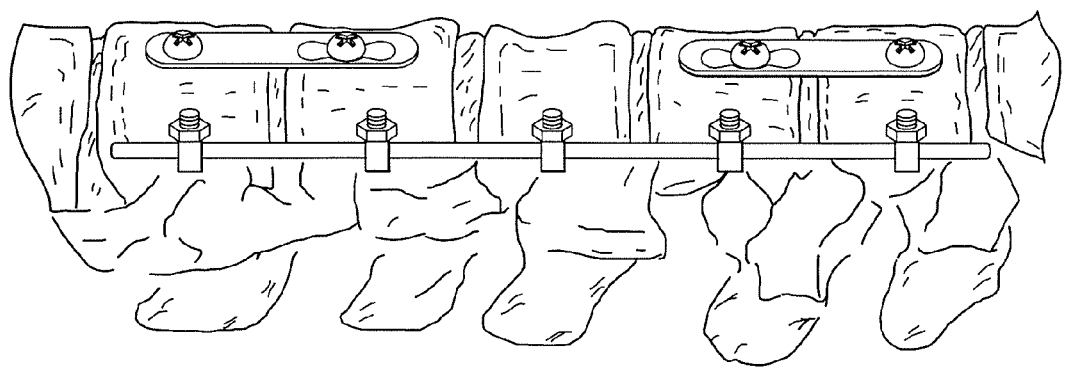
FIG. 12 is a representation of the thoracolumbar spine with another embodiment of a rod-plate anterior system that has a lower profile compared to the embodiment illustrated in FIG. 5.
Figure 13A:
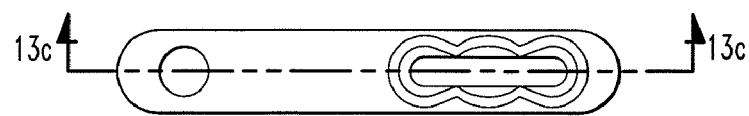
FIG. 13a is a top view of a rectangular spinal plate.
Figure 13B:
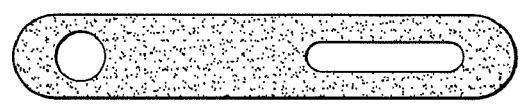
FIG. 13b is a bottom view of a rectangular spinal plate.
Figure 13C:
Figure 13D:
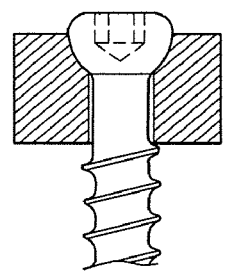
FIG. 13d is a cross-sectional view of a bone screw with the spinal plate connection, as illustrated in FIG. 12.

For the purposes of promoting an understanding of the principles of the invention, reference will now be made to certain embodiments thereof and specific language will be used to describe the same. It will nevertheless be understood that no limitation of the scope of the invention is thereby intended, such alterations, further modifications and further applications of the principles of the invention as described herein being contemplated as would normally occur to one skilled in the art to which the invention relates.

The present invention provides numerous advantages over a dual rod system, including fewer parts and a lower profile, accommodation of spinal deformity, ease in applying implants to a severely deformed spine, ease in adjusting the end vertebrae to avoid wedging and/or degeneration of disc caudal of the last screw, usable from the thoracic spine to the lumbar spine, reduced operation times and simplification of the operational steps.

In preferred embodiments, the invention includes an anterior spinal instrumented method of treating spinal deformities, the spine having a convex side and a concave side, the method comprising the following steps: on the convex side of the deformity, attaching two spinal plates to cephalad and caudal end vertebrae respectively; fixing a rod anterior system on the posterior portion of the convex side; attaching two spinal plates on the most cephalad and caudal end vertebrae through the vertebral screws of the single-rod anterior system; and the deformity of the spine is corrected through compression, distraction and derotation of the rod anterior system. The method may further include inserting several cancellous screws into the cephalad and caudal end vertebrae and their adjacent vertebrae at the anterior portion of the convex side through the spinal plate which is connected to the rod spinal instrumentation.

This preferred method may also include a spinal plate which has an "L" shape that connects at least two vertebrae, and which comprises: a first end and a second end, where the first end has a longitudinal portion and a length sufficient to span between two vertebrae. The longitudinal portion has an elongated slot which has a series of openings for receiving screws such that the plate can be attached to the vertebrae. The openings allow the force transmitting members to be positioned on the vertebra where desired and enables the spinal plate to be used with different sized vertebrae.

The second end of the spinal plate has a transverse portion that is vertical with the longitudinal portion. The transverse portion fits together with the lateral side of the vertebra in an anterior-posterior direction. In the superior-inferior direction, the plate's thickness is narrowed to avoid endplate prominence and so that the plate fits closely to the bone. The transverse portion has a first aperture in the anterior region and a second aperture in the posterior region. The second aperture is located in the middle point of the superior inferior direction, which indicates that the spinal screw is safely in the middle position. The first aperture is angled towards the center allowing the screw to be inserted in the posterior direction to avoid damaging the aorta and disrupting the front edge of the vertebral body. The two-hole design provides a stable triangular screw construct in the vertebrae between the two screws and the transverse portion of the spinal plate. Different angles are designed from 80° to 100° between the longitudinal portion and the transverse portion of the spinal plate so that the spinal plate can accommodate different spinal deformities. Different lengths are designed for the longitudinal portion of the spinal plate so the spinal plate can span at least two vertebrae.

On the bottom side surface and top side surface, the spinal plate has a bottom side surface for facing the vertebrae. In the longitudinal portion, pluralities of serrations are formed along the slot. The serrations prevent sliding of the spinal plate relative to the vertebrae. In the transverse direction, the spinal plate is slightly concave in shape so that it matches the vertebral anatomy for optimum anatomic fit and to minimize the construct profile in the anterior-posterior direction. On the top surface, in the longitudinal portion, the slot is provided with a beveled upper or outer edge portion, which slopes at the same angle as the lower rounded surface of the head portion of cancellous screw. A plurality of recesses is provided in the beveled edge portions to engage the lower rounded surface of the cancellous screw. The recesses hold the screw against sidewise movement relative to the spinal plate. The recesses are defined by surfaces, which form a portion of a cone having the same included angle as the lower round surface of the screw head. In the transverse portion, an anterior hole is provided with a beveled upper edge portion, which slopes at the same angle as the lower rounded surface of the screw head. The topside surface of the transverse portion is slightly convex in anterior-posterior direction so that it matches the vertebral anatomy.

The cancellous screw may also include a bone engaging portion having cancellous threads thereon, and may include a head portion. The head portion includes a lower rounded surface and an upper rounded surface. A generally cylindrical portion separates the lower rounded surface and the upper rounded surface. The screw head also includes a tool-engaging recess. The tool-engaging recess may be of any suitable configuration, including hexagonal, hexalobed, or any other appropriate configuration. The rod anterior system may be any suitable single-rod anterior system including, for example, TSRH, CDH, Miami, or any others.

In practice of the preferred method, the spinal plate may also be of a rectangle-shape that connects at least two vertebrae through a pair of similar upper and lower vertebral staples. The staples comprise a first end and a second end. The first end has a first hole and the second end has an elongated u-shaped slot. The plate also includes a bottom side surface (the screw-facing side) and top side surface (the washer-facing side). On the bottom side surface, the first hole defines a plurality of serrations extending radially about the hole so that the spinal plate can mount to a cancellous screw in varying angular orientations. On the top side surface, the elongated u-shaped slot defines a plurality of parallel serrations so that the spinal plate may be placed in a variable position to match the adjacent bone screw through a rectangle-serrated washer. Using this plate, a pair of similar upper and lower vertebral staples may be attached to both end vertebrae of the instrumentation segment.

The vertebral staples also include a posterior hole and an anterior hole. The posterior hole receives the screws of the anterior rod system, and the anterior hole receives a cancellous screw for the spinal plate fixation. The vertebral staple is wedge-shaped and is capable of securing a pair of metal tensioning cables to a vertebra via spinal screws. The staple preferably comprises three prongs, a pair of substantially parallel and perpendicularly offset laminar posterior legs which are inserted into the vertebral endplates, the parallel distance between the posterior legs being such as to fit snugly over either side of a vertebra. The third prong is located in central position of the staple to avoid damaging the aorta and thoracic-abdominal organs.

The staple may further include a pair of spinal screw receiving apertures. The posterior hole is located in the middle portion between the two posterior staple prongs, which positions the spinal screw safely in the middle position. The anterior hole is inclined towards the center of the anterior portion of the staple. The anterior hole geometrically allows the anterior screw to be directed posterior to avoid damaging the aorta and disrupting the front edge of the vertebral body for good purchase. The posterior hole allows the posterior vertebral screw to be directed anteriorly to avoid injury of the spinal cord. The two-hole design provides a stable triangular screw construct in the vertebra between the two screws and the staple.

The staple further comprises an integral substantially solid and wedge-shaped laminal bridge portion which is slightly convex in shape so that it matches the vertebral anatomy for optimum anatomic fit to minimize the construct profile in the anterior-posterior direction. The portion of the superior-inferior direction is narrower than the two posterior prongs to avoid endplate prominences and to allow the plate to fit closely to the bone.

As a template to start a hole for screw insertion, the vertebral staple increases the screw pullout force and has been shown to be very effective in preventing screw migration and screw pullout. Different sizes and shapes accommodate a variety of anatomical shapes of vertebra so as to allow the lateral plates to be fixed to either lumbar or thoracic vertebrae.

In the preferred method, the cancellous screw may receive the rectangle-shaped spinal plate via the anterior hole of the staple, which comprises a first end and a second end. The first end has an insertion tip with cancellous thread extending from the insertion tip along a substantial portion of the first end. The second end is defined as a protruding shaft extending outwardly from said first end with at least a portion of said protruding shaft threaded. The protruding shaft has the same diameter as the first end. The second end also includes a tool-engaging recess. The tool-engaging recess may be of any suitable configuration, including hexagonal, hexalobed, or any other suitable configuration. A wall junction is formed between the first end and second end. There are radial serrations on the top surface of the wall junction in the most end cancellous screw, but a plain top surface of the wall junction in the adjacent most end cancellous screw. The radial serrations allow the spinal plate to match the adjacent vertebral screw.

The preferred method may also include embodiments in which the rectangle-serrated washer is a rectangle-shaped washer. The washer comprises a bottom side surface defined by a plurality of parallel serrations so that the washer can mount to the lateral plate to lock the anterior screw. The topside surface may be plain to receive the nut, and the washer may further include an aperture in the central position. The rectangle-shaped spinal plate may also have a sufficient length to cover more vertebrae, even from cephalad to caudal vertebrae of the instrumented segment.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all publications cited herein are indicative of the abilities of those of ordinary skill in the art and are hereby incorporated by reference in their entirety as if individually incorporated by reference and fully set fourth.

What is claimed is:

1. A method of treating a spinal deformity having a convex side and a concave side, the method comprising the steps of:
    attaching first and second spinal plates to cephalad and caudal end vertebrae, respectively;
    fixing a rod system along the deformity using vertebral screws, wherein the first and second spinal plates are attached to the cephalad and caudal end vertebrae, respectively, by at least one of the vertebral screws;
    correcting the spinal deformity through at least one of compression, distraction and derotation of the rod system;
    securing the first spinal plate to a first vertebra adjacent the cephalad end vertebra using a first bone anchor; and
    securing the second spinal plate to a second vertebra adjacent the caudal end vertebra using a second bone anchor.

2. The method of claim 1, wherein the first and second spinal plates are "L" shaped, and each comprises:
    a first end portion and a second end portion, a bottom surface for facing the vertebra and a top surface;
    the first end portion comprising a longitudinal portion and a length sufficient to span between two vertebrae, wherein the longitudinal portion includes an elongated slot providing a series of openings for receiving screws such that the plate can be attached to the vertebrae, wherein the openings are configured to allow the screws to be positioned on the vertebra where desired and to accommodate different sized vertebrae, a plurality of serrations formed along the bottom portion of the slot, configured to prevent sliding of the spinal plate relative to the vertebrae, a beveled upper or outer edge portion of the slot, which conforms to a lower rounded surface of a head portion of a cancellous screw, and wherein a plurality of recesses is provided in the beveled edge portions to engage the lower rounded surface of the cancellous screw, effective to hold the screw against sidewise movement relative to the spinal plate, and wherein the recesses are defined by surfaces which form a portion of a cone having the same included angle as the lower round surface of the screw head;

the second end portion comprising a transverse portion that is configured to fit together with the lateral side of the vertebra in an anterior-posterior direction during use, wherein in the superior-inferior direction a thickness of the plate is narrowed to avoid endplate prominence and so that the plate fits closely to the bone;

the transverse portion comprises a first aperture in the anterior region and a second aperture in the posterior region, wherein the second aperture is located in the middle point of the superior-inferior direction, and the first aperture is angled towards the center allowing a screw to be inserted in the posterior direction to avoid damaging the aorta and disrupting the front edge of the vertebral body during use, and providing a stable triangular screw construct in the vertebrae between the two screws and the transverse portion of the spinal plate;

wherein the bottom surface is slightly concave in shape so as to match the vertebral anatomy for optimum anatomic fit and minimizes the construct profile in an anterior-posterior direction; and wherein the top surface transverse portion forms an anterior hole configured with a beveled upper edge portion which conforms to the lower rounded surface of a screw head and wherein the topside surface of the transverse portion is slightly convex in anterior-posterior direction to match the vertebral anatomy.

3. The method of claim 2, wherein the angle between the longitudinal portion and the transverse portion is from 80° to 100°.

4. The method of claim 2, wherein the length of the longitudinal portion is sufficient to span more than two vertebrae.

5. The method of claim 1, wherein the spinal plate is configured in a rectangle-shape that connects at least two vertebrae through a pair of similar upper and lower vertebral staples, the plate comprising:

a first end and second end, the first end forming a hole and the second end forming an elongated slot;

a bottom side surface configured to face the screw, and a top side surface configured to face a washer, wherein the perimeter of the hole on the bottom surface comprises a plurality of serrations extending radially about the hole so that the spinal plate can mount to a cancellous screw in varying angular orientations during use, and wherein the top side surface in the vicinity of the elongated slot provides a plurality of parallel serrations effective to place the spinal plate in a variety of positions to match the adjacent bone screw through a rectangular, serrated washer.

6. The method of claim 5, wherein the rectangular-serrated washer comprises:

a bottom side surface comprising a plurality of parallel serrations configured to mount to the lateral plate to lock the anterior screw; and a topside surface configured to receive a nut.

7. The method of claim 5, comprising a rectangular spinal plate configured to connect at least two vertebrae without use of upper and lower vertebral staples, the plate comprising:

a first end portion providing an aperture and a second end portion forming a series of openings for receiving bone screws, wherein a plurality of serrations are formed along the bottom of the plate, and wherein the top edges of the openings are beveled to conform to the lower rounded surface of the head portion of a cancellous screw.

8. The method of claim 1, wherein a pair of similar upper and lower vertebral staples are attached to both the cephalad and caudal end vertebrae, wherein the vertebral staples form a posterior hole and an anterior hole;

wherein the posterior hole is configured to receive a screw of the rod system, and the anterior hole is configured to receive a cancellous screw for the spinal plate fixation; and wherein a vertebral staple is wedge-shaped and capable of securing a pair of metal tensioning cables to a vertebra via spinal screws;

wherein the vertebral staples comprise two laterally extending members, one extending from each side of the staple in parallel relation to each other, wherein the distance between the laterally extending members is configured to fit snugly over either side of a vertebra during use;

wherein the vertebral staple comprises a third member perpendicular to the first and second members and located in the central position of the staple to avoid damaging the aorta and thoracic-abdominal organs during use;

wherein the vertebral staple forms an anterior aperture and a posterior aperture configured to receive a spinal screw, wherein the posterior aperture is formed in the central portion of the staple between the laterally extending members and inclined toward the center of the anterior portion of the staple, the aperture forming portion being configured to allow an anterior screw to be directed in a posterior direction to avoid damaging the aorta and disrupting the front edge of the vertebral body for good purchase during use, the posterior aperture forming portion being configured to allow a posterior vertebral screw to be directed in an anterior direction to avoid the injury to a spinal cord during use, wherein the anterior and posterior apertures are configured to provide a stable triangular screw construct in the vertebra between the two screws and the staple during use;

wherein the vertebral staple comprises an integral substantially solid and wedge shaped laminal bridge portion which is slightly convex in shape, configured to match the vertebral anatomy for optimum anatomic fit and to minimize the construct profile of the anterior-posterior direction, wherein the superior-inferior portion is narrower than the portion adjoining the laterally extending members to avoid endplate prominences and to fit the plate fit closely to the bone during use.

9. The method of claim 8, wherein the vertebral staple is configured to be fixed to a lumbar vertebra.

10. The method of claim 8, wherein the vertebral staple is configured to be fixed to a thoracic vertebra.

11. The method of claim 8, comprising inserting a cancellous screw through the anterior hole of the staple, the cancellous screw comprising:

a first end and a second end, the first end comprising an insertion tip with cancellous thread extending from the insertion tip along a substantial portion of the first end, the second comprising a shaft extending from the first end in the direction opposite the insertion tip, wherein at least a portion of the shaft is threaded and wherein the end of the shaft provides a tool engaging recess; and a wall junction formed between the first end and second end.

12. The method of claim 11, wherein the wall junction comprises radial serrations on the top surface thereof.

13. The method of claim 11, wherein the tool engaging recess is hexagonal or hexalobed.

14. The method of claim 8, wherein the laterally extending members each terminate in an offset laminar posterior leg configured to be inserted into vertebral endplates during use.

15. The method of claim 1, wherein the securing of the first spinal plate to the first vertebra comprises inserting a first cancellous screw through an opening in the first spinal plate and into engagement with the first vertebra, and wherein the securing of the second spinal plate to the second vertebra comprises inserting a second cancellous screw through an opening in the second spinal plate and into engagement with the second vertebra.

16. The method of claim 15, wherein the openings in the first and second spinal plates comprise elongated slots.

17. The method of claim 16, wherein the cancellous screws each include a bone engaging portion having cancellous threads thereon, and a head portion;

the head portion comprising a lower rounded surface and an upper rounded surface, and wherein a generally cylindrical portion separates the lower rounded surface and the upper rounded surface and comprising a tool-engaging recess.

18. The method of claim 17, wherein the tool-engaging recess is hexagonal or hexalobed.

19. The method of claim 1, wherein the attaching of the first and second spinal plates to the cephalad and caudal end vertebrae comprises attaching of the first and second spinal plates along the convex side of the deformity, and wherein the fixing of the rod system comprises fixing of the rod system along the convex side of the deformity.

20. The method of claim 1, wherein the fixing of the rod system along the deformity comprises fixing of the rod system along a posterior portion of the deformity, wherein the securing of the first spinal plate to the first vertebra comprises securing of the first spinal plate to an anterior portion of the first vertebra, and wherein the securing of the second spinal plate to the second vertebra comprises securing of the second spinal plate to an anterior portion of the second vertebra.

21. A method of treating a deformity of the spinal column having a convex side and a concave side, comprising:

providing first and second spinal plates, a spinal rod, a first set of bone anchors, and a second set of bone anchors;

anchoring the spinal rod to the spinal column along the convex side of the deformity using the first set of bone anchors;

attaching the first spinal plate to a first vertebra along the convex side of the deformity and coupling the first spinal plate with the spinal rod;

attaching the second spinal plate to a second vertebra along the convex side of the deformity and coupling the second spinal plate with the spinal rod;

correcting the spinal deformity through at least one of compression, distraction and derotation of the spinal rod;

securing the first spinal plate to the first vertebra and to an adjacent third vertebra using a number of the second set of bone anchors; and securing the second spinal plate to the second vertebra and to an adjacent fourth vertebra using a number of the second set of bone anchors.

22. The method of claim 21, wherein the attaching and coupling of the first spinal plate comprises engaging at least one of the first set of bone anchors with the first spinal plate; and wherein the attaching and the coupling of the second spinal plate comprises engaging at least one of the first set of bone anchors with the second spinal plate.

23. The method of claim 21, wherein the attaching and coupling of the first spinal plate comprises inserting at least one of the first set of bone anchors through an opening in the first spinal plate and into engagement with the first vertebra; and wherein the attaching and coupling of the second spinal plate comprises inserting at least one of the first set of bone anchors through an opening in the second spinal plate and into engagement with the second vertebra.

24. The method of claim 21, wherein the securing of the first spinal plate to the first vertebrae comprises inserting one of the second set of bone anchors through a first opening in the first spinal plate and into engagement with the first vertebra; and wherein the securing of the second spinal plate to the second vertebra comprises inserting one of the second set of bone anchors through a second opening in the second spinal plate and into engagement with the second vertebra.

25. The method of claim 24, wherein the securing of the first spinal plate to the third vertebra comprises inserting one of the second set of bone anchors through a third opening in the first spinal plate and into engagement with the first vertebra; and wherein the securing of the second spinal plate to the fourth vertebra comprises inserting one of the second set of bone anchors through a fourth opening in the second spinal plate and into engagement with the fourth vertebra.

26. A method of treating a spinal deformity, comprising:
providing a spinal rod and first and second spinal plates;
anchoring the spinal rod along the spinal deformity;
attaching the first spinal plate to a first vertebra along the deformity and coupling the first spinal plate with the spinal rod;
attaching the second spinal plate to a second vertebra along the deformity and coupling the second spinal plate with the spinal rod;
reducing the spinal deformity through at least one of compression, distraction and derotation of the spinal rod; and
maintaining the spinal deformity in a reduced condition by coupling the first vertebra to an adjacent third vertebra and coupling the second vertebra to an adjacent fourth vertebra, wherein the coupling of the first vertebra to the adjacent third vertebra comprises securing the first spinal plate to each of the first and third vertebrae, and wherein the coupling of the second vertebra to the adjacent fourth vertebra comprises securing the second spinal plate to each of the second and fourth vertebrae.

27. The method of claim 26, wherein the anchoring of the spinal rod along the spinal deformity comprises engaging a plurality of bone screws to a plurality of vertebrae; and wherein the attaching and coupling of the first spinal plate comprises inserting at least one of the bone screws through an opening in the first spinal plate and into engagement with the first vertebra; and wherein the attaching and coupling of the second spinal plate comprises inserting at least one of the bone screws through an opening in the second spinal plate and into engagement with the second vertebra.

28. A method of treating a spinal deformity, comprising:
providing a spinal rod and first and second spinal plates;
anchoring the spinal rod along the spinal deformity;
attaching the first spinal plate to a first vertebra along the deformity and coupling the first spinal plate with the spinal rod;
attaching the second spinal plate to a second vertebra along the deformity and coupling the second spinal plate with the spinal rod;
reducing the spinal deformity through at least one of compression, distraction and derotation of the spinal rod; and
maintaining the spinal deformity in a reduced condition by coupling the first vertebra to an adjacent third vertebra and coupling the second vertebra to an adjacent fourth vertebra, wherein the coupling of the first vertebra to the adjacent third vertebra comprises engaging a third spinal plate to the first and third vertebrae, and wherein the coupling of the second vertebra to the adjacent fourth vertebra comprises engaging a fourth spinal plate to the second and fourth vertebrae.

29. The method of claim 28, wherein the anchoring of the spinal rod along the spinal deformity comprises engaging a plurality of bone screws to a plurality of vertebrae; and
wherein the attaching and coupling of the first spinal plate comprises inserting at least one of the bone screws through an opening in the first spinal plate and into engagement with the first vertebra; and
wherein the attaching and coupling of the second spinal plate comprises inserting at least one of the bone screws through an opening in the second spinal plate and into engagement with the second vertebra.

30. A method of treating a spinal deformity, comprising:
providing a spinal rod and first and second spinal plates;
anchoring the spinal rod along the spinal deformity;
attaching the first spinal plate to a first vertebra along the deformity and coupling the first spinal plate with the spinal rod;
attaching the second spinal plate to a second vertebra along the deformity and coupling the second spinal plate with the spinal rod;
reducing the spinal deformity through at least one of compression, distraction and derotation of the spinal rod; and
maintaining the spinal deformity in a reduced condition by coupling the first vertebra to the second vertebra, wherein the coupling of the first vertebra to the second vertebra comprises engaging a third spinal plate to each of the first and second spinal plates.

31. A method of treating a spinal deformity, comprising:
providing a spinal rod and first and second spinal plates;
anchoring the spinal rod along the spinal deformity;
attaching the first spinal plate to a first vertebra along the deformity and coupling the first spinal plate with the spinal rod;
attaching the second spinal plate to a second vertebra along the deformity and coupling the second spinal plate with the spinal rod;
reducing the spinal deformity through at least one of compression, distraction and derotation of the spinal rod; and
maintaining the spinal deformity in a reduced condition by coupling the first vertebra and the second vertebra to one or more other vertebrae by anchoring one or more elongate elements other than the spinal rod to the first and second vertebrae and to the other vertebrae, and wherein the one or more elongate elements comprises a plate anchored to the first and second vertebrae and to the other vertebrae.

32. The method of claim 31, wherein the anchoring of the spinal rod along the spinal deformity comprises engaging a plurality of bone screws to a plurality of vertebrae; and
wherein the attaching and coupling of the first spinal plate comprises inserting at least one of the bone screws through an opening in the first spinal plate and into engagement with the first vertebra; and
wherein the attaching and coupling of the second spinal plate comprises inserting at least one of the bone screws through an opening in the second spinal plate and into engagement with the second vertebra.

33. The method of claim 31, wherein the spinal deformity has a convex side and a concave side; and
wherein the anchoring of the spinal rod comprises anchoring along the convex side of the spinal deformity; and
wherein the attaching of the first spinal plate to the first vertebra comprises attaching along the convex side of the spinal deformity; and
wherein the attaching of the second spinal plate to the second vertebra comprises attaching along the convex side of the spinal deformity.

34. The method of claim 31, wherein the reducing of the spinal deformity is accomplished through at least one of compression, distraction and derotation of the spinal rod.

* * * * *

UNITED STATES PATENT AND TRADEMARK OFFICE
CERTIFICATE OF CORRECTION

PATENT NO. : 7,658,754 B2
APPLICATION NO. : 11/368001
DATED : February 9, 2010
INVENTOR(S) : Zhang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 666 days.

Signed and Sealed this

Thirtieth Day of November, 2010

David J. Kappos
*Director of the United States Patent and Trademark Office*